(12) United States Patent
Hungerford et al.

(10) Patent No.: US 9,144,644 B2
(45) Date of Patent: Sep. 29, 2015

(54) INFUSION PUMP WITH INDEPENDENTLY CONTROLLABLE VALVES AND LOW POWER OPERATION AND METHODS THEREOF

(75) Inventors: Roger L. Hungerford, Medina, NY (US); Tuan Bui, Buffalo, NY (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 1079 days.

(21) Appl. No.: 13/196,136

(22) Filed: Aug. 2, 2011

(65) Prior Publication Data

US 2013/0035659 A1 Feb. 7, 2013

(51) Int. Cl.
*A61M 1/00* (2006.01)
*A61M 5/14* (2006.01)
*A61M 5/142* (2006.01)
*A61M 5/168* (2006.01)
*A61M 5/172* (2006.01)

(52) U.S. Cl.
CPC .............. *A61M 5/14* (2013.01); *A61M 5/14228* (2013.01); *A61M 5/16813* (2013.01); *A61M 5/172* (2013.01); *A61M 2205/3334* (2013.01)

(58) Field of Classification Search
CPC ................ A61M 2205/3334; A61M 5/16813; A61M 5/172; A61M 5/168; A61M 5/1411; A61M 2005/14208
USPC ........................................................ 604/118
See application file for complete search history.

(56) References Cited

U.S. PATENT DOCUMENTS

| | | |
|---|---|---|
| 4,321,461 A | 3/1982 | Walter, Jr. et al. |
| 4,328,801 A | 5/1982 | Marx et al. |
| 4,504,263 A | 3/1985 | Steuer et al. |
| 4,525,163 A | 6/1985 | Slavik et al. |
| 4,558,996 A | 12/1985 | Becker |
| 4,583,975 A | 4/1986 | Pekkarinen et al. |
| 4,634,426 A | 1/1987 | Kamen |
| 4,673,820 A | 6/1987 | Kamen |
| 4,680,977 A | 7/1987 | Conero et al. |
| 4,820,281 A | 4/1989 | Lawler, Jr. |
| 4,838,856 A | 6/1989 | Mulreany et al. |

(Continued)

FOREIGN PATENT DOCUMENTS

| | | |
|---|---|---|
| DE | 4205718 | 8/1992 |
| EP | 0554716 | 12/1997 |

(Continued)

*Primary Examiner* — Kevin C Sirmons
*Assistant Examiner* — Deanna K Hall
(74) *Attorney, Agent, or Firm* — Greer, Burns & Crain, Ltd.

(57) ABSTRACT

An infusion pump, including: a specially programmed microprocessor; a drip chamber for connection to a source of fluid and to an output tubing; a pumping section including a plurality of fingers and a first actuator, controllable using the microprocessor, for sequentially displacing the plurality of finger to compress a first portion of the output tubing to displace fluid from the drip chamber through the output tubing; an inlet valve disposed between the drip chamber and the pumping section and arranged to compress the output tubing to restrict or block flow through the output tubing; and a second actuator, controllable using the microprocessor, for opening or closing the inlet valve independent of the displacement of the plurality of fingers; or for operating the inlet valve to control a rate of flow of fluid from the drip chamber to the portion of the output tubing.

20 Claims, 9 Drawing Sheets

(56) References Cited

U.S. PATENT DOCUMENTS

| | | |
|---|---|---|
| 4,909,786 A | 3/1990 | Gijselhart et al. |
| 4,936,828 A | 6/1990 | Chiang |
| 5,006,050 A | 4/1991 | Cooke et al. |
| 5,045,069 A | 9/1991 | Imparato |
| 5,057,076 A | 10/1991 | Polaschegg |
| 5,057,090 A | 10/1991 | Bessman |
| 5,320,503 A | 6/1994 | Davis |
| 5,331,309 A | 7/1994 | Sakai |
| 5,357,827 A | 10/1994 | Natwick et al. |
| 5,364,364 A | 11/1994 | Kasvikis et al. |
| 5,366,346 A | 11/1994 | Danby |
| 5,415,641 A | 5/1995 | Yerlikaya et al. |
| 5,534,691 A | 7/1996 | Holdaway et al. |
| 5,542,826 A | 8/1996 | Warner |
| 5,554,013 A * | 9/1996 | Owens et al. ............ 417/413.1 |
| 5,562,615 A | 10/1996 | Nassif |
| 5,658,133 A | 8/1997 | Anderson et al. |
| 5,803,712 A | 9/1998 | Davis et al. |
| 5,899,665 A | 5/1999 | Makino et al. |
| 6,049,381 A | 4/2000 | Reintjes et al. |
| 6,083,206 A | 7/2000 | Molko |
| 6,149,631 A | 11/2000 | Haydel, Jr. |
| 6,159,186 A | 12/2000 | Wickham et al. |
| 6,213,738 B1 | 4/2001 | Danby et al. |
| 6,394,771 B2 | 5/2002 | Butterfield |
| 6,562,012 B1 | 5/2003 | Brown et al. |
| 6,629,955 B2 | 10/2003 | Morris et al. |
| 6,736,801 B1 | 5/2004 | Gallagher |
| 6,984,052 B1 | 1/2006 | Del Castillo |
| 7,044,002 B2 | 5/2006 | Ericson et al. |
| 7,066,915 B2 | 6/2006 | Olsen |
| 7,190,275 B2 | 3/2007 | Goldberg et al. |
| 7,255,683 B2 | 8/2007 | Vanderveen et al. |
| 7,309,333 B2 | 12/2007 | Mason |
| 7,635,351 B2 | 12/2009 | Peter |
| 7,695,448 B2 | 4/2010 | Cassidy et al. |
| 7,767,991 B2 | 8/2010 | Sacchetti |
| 7,892,204 B2 | 2/2011 | Kraus |
| 7,918,834 B2 | 4/2011 | Mernoe et al. |
| 2003/0045840 A1 | 3/2003 | Burko |
| 2006/0291211 A1 | 12/2006 | Rodriguez et al. |
| 2008/0004574 A1 | 1/2008 | Dyar et al. |
| 2008/0051732 A1 | 2/2008 | Chen |
| 2010/0309005 A1 | 12/2010 | Warner et al. |
| 2011/0158823 A1 | 6/2011 | Wang et al. |
| 2012/0013735 A1 | 1/2012 | Tao |

FOREIGN PATENT DOCUMENTS

| | | |
|---|---|---|
| JP | 5195959 | 8/1993 |
| WO | 0240084 | 5/2002 |
| WO | 2004037322 | 5/2004 |
| WO | 2007033025 | 3/2007 |
| WO | 2009039203 | 3/2009 |

* cited by examiner

| Flow pulse (sec) | No. of flow pulses per hr. | Amount of fluid per flow packet micro L | Instantaneous rate micro L/hr |
|---|---|---|---|
| 2 | 164 | 0.61 | 0.31 |
| 4 | 150 | 0.67 | 0.17 |
| 6 | 138 | 0.72 | 0.12 |
| 8 | 129 | 0.78 | 0.10 |
| 10 | 120 | 0.83 | 0.08 |
| 12 | 113 | 0.89 | 0.07 |
| 14 | 106 | 0.94 | 0.07 |
| 16 | 100 | 1.00 | 0.06 |
| 18 | 95 | 1.06 | 0.06 |

Fig. 4

INFUSION PUMP WITH INDEPENDENTLY CONTROLLABLE VALVES AND LOW POWER OPERATION AND METHODS THEREOF

TECHNICAL FIELD

The present disclosure relates to an infusion pump with an independently controllable inlet valve. The present disclosure also relates to an infusion pump with an inlet valve for controlling flow from a drip chamber. The present disclosure further relates to an infusion pump switchable between gravity-feed operation and active pumping operation.

BACKGROUND

FIG. 9 is a schematic representation of prior art peristaltic pump 10. Pump includes drip chamber 12 connected to source of fluid 14, tubing 16 connected to the drip chamber, upstream valve 18 to block or allow fluid flow from the drip chamber to the tubing, and a plurality of fingers 20 to create a moving zone of occlusion along the tubing and to push the fluid downstream past downstream valve 22. The downstream valve is used to block or enable fluid output, for example, blocking fluid output when the upstream valve is opened. The upstream valve, fingers and downstream valves are typically engaged with cam lobes 24 on cam shaft 26 and rotated by motor and associated gears 28. Different shapes for the cam lobes determine the timing of opening and closing of the upstream and downstream valves and peristaltic function of the fingers. In general a pumping cycle for the pump is as follows: a first cam lobe operates the upstream valve to fully open the upstream valve to admit a volume of fluid while a second cam lobe operates the outlet valve to close the downstream valve; the first cam lobe operates to close the inlet valve and the second cam lobe operates to fully open the downstream valve; a set of cam lobes operates on the fingers such that the fingers expel fluid past the downstream valve; the second cam lobe operates on the downstream valve to close the downstream valve; and, the preceding sequence is repeated.

A typical maximum volume for the tubing between the upstream and downstream valves is 0.160 milliliter. Often the maximum volume is reduced due to the fingers partially compressing the tubing, for example, the maximum volume is reduced to 0.080 milliliter. Since the upstream and downstream valves and fingers are all mounted on a single cam shaft, it is not possible to control the amount of fluid entering the tubing independently from the movements of the fingers. The amount of fluid entering the tubing from the drip chamber is controlled by the opening and closing of the upstream valve, thus is not possible to control the amount of fluid entering the chamber, independently from the movements of the fingers. That is, for each pump cycle, the upstream valve is fully opened and an amount of fluid equal to the maximum volume flows to the tubing from the drip chamber. Therefore, the minimum amount of fluid entering the pumping chamber at each pumping cycle is 0.080 milliliter in this case.

Certain infusion regimens require very low flow rates, for example, 0.1 microliter/hour. Pump 10 has difficulty in maintaining flow continuity at such low flow rates.

Cam shaft 26 is supported proximate each end by respective bearings 30. The bearings hold the shaft in a position that is fixed except for rotation of the shaft. The fixed position is such that cam lobes 24 are able to operate fingers 14 and to open and close the upstream and downstream valves. In general, the cam lobes are positioned such that one of the upstream or downstream valves is closed at all times. One possible mode of failure for pump 10 is the failure of some or all of bearings 30. For example, the bearings can fail such that the shaft is no longer held in the fixed position noted above and one or both of the ends of the shaft are further from body. In this case, the cam lobes may be far enough from the fingers and/or the upstream or downstream valves such that the cam lobes are no longer able to close the upstream and/or downstream valves. Thus, for failure of some or all of the bearings, pump 10 is unable to control flow from the drip chamber. For example, in the sequence noted above, when the upstream valve is opened it is presumed that the downstream valve is closed. However, if the bearing failure results in the cam shaft being unable to close the downstream valve, an uncontrolled flow from the drip chamber results when the upstream valve is opened. An uncontrolled flow condition can be extremely hazardous to a patient receiving an infusion via pump 10, for example, resulting in a dangerously high dosage of a drug being infused with pump 10.

FIG. 10 is a schematic representation of a prior art gravity-feed infusion arrangement. In some clinical applications, fluid delivery by gravity, as shown in FIG. 10, is acceptable. For delivery by gravity, gravity force is strong enough to cause fluid to flow from container 32 hung on pole 34 through tubing 36 to the patient. However, the flow rate from container 32 cannot be automatically controlled and it is difficult to accurately control the flow rate. For example, roller clamp 38 is used to manually control the flow. The clamp is equipped with roller 40 that may be rolled by hand to contract tubing 14 to compress the tubing to control the flow through the tubing from container 32. Such manual control is not accurate and is very susceptible to human error.

SUMMARY

According to aspects illustrated herein, there is provided an infusion pump, including: a specially programmed microprocessor; a drip chamber for connection to a source of fluid and to an output tubing; a pumping section including a plurality of fingers and a first actuator, controllable using the microprocessor, for sequentially displacing the plurality of finger to compress a first portion of the output tubing to displace fluid from the drip chamber through the output tubing; an inlet valve disposed between the drip chamber and the pumping section and arranged to compress the output tubing to restrict or block flow through the output tubing; and a second actuator, controllable using the microprocessor, for opening or closing the inlet valve independent of the displacement of the plurality of fingers; or for operating the inlet valve to control a rate of flow of fluid from the drip chamber to the portion of the output tubing.

According to aspects illustrated herein, there is provided an infusion pump, including: a specially programmed microprocessor; a drip chamber for connection to a source of fluid and to an output tubing; a flow sensor for measuring flow; a pumping section including a plurality of fingers, an outlet valve, and a first actuator for sequentially displacing the plurality of finger to displace fluid through the output tubing; an inlet valve disposed between the pumping section and the drip chamber; and a second actuator. For detection, by the flow sensor, of flow above a predetermined level, the microprocessor is for closing the outlet valve independently of the inlet valve using the first actuator, and closing the inlet valve independently of the outlet valve using the second actuator.

According to aspects illustrated herein, there is provided an infusion pump, including: a specially programmed microprocessor; a drip chamber for connection to a source of fluid and to an output tubing; a flow sensor; a pumping section including a plurality of fingers, an outlet valve, and a first actuator for controlling operation of the plurality of fingers and the outlet valve; an inlet valve disposed between the pumping section and the drip chamber; and a second actuator for operating the inlet valve. In a gravity-feed mode the microprocessor: controls the first actuator to maintain the plurality of fingers in respective fixed positions and to at least partially open the outlet valve such that a passageway is formed in the output tubing from the drip chamber past the outlet valve; and controls the second actuator, using data from the flow sensor including flow measured by the flow sensor, to operate the inlet valve to establish flow from the drip chamber to the output tubing at a desired flow rate. In an active pumping mode, the microprocessor: controls the second actuator to open and close the inlet valve; and controls the first actuator to operate the plurality of fingers to displace fluid through the output tubing at the desired flow rate.

According to aspects illustrated herein, there is provided an infusion pump, including: a specially programmed microprocessor; a drip chamber for connection to a source of fluid and to an output tubing; a flow sensor for measuring flow through the drip chamber from the source of fluid; an inlet valve disposed after the drip chamber; and an actuator for operating the inlet valve. In a gravity-feed mode the microprocessor: controls the actuator, using data from the flow sensor including flow measured by the flow sensor, to operate the inlet valve to establish flow from the drip chamber to the output tubing at a desired flow rate.

According to aspects illustrated herein, there is provided an infusion pump, including: a specially programmed microprocessor; a drip chamber for connection to a source of fluid and to an output tubing; a flow sensor for measuring flow through the drip chamber from the source of fluid; an element to force fluid out of the source of fluid; an inlet valve disposed after the drip chamber; and an actuator for operating the inlet valve. In a gravity-feed mode the microprocessor: controls the actuator, using data from the flow sensor including flow measured by the flow sensor, to operate the inlet valve to establish flow from the drip chamber to the output tubing at a desired flow rate.

According to aspects illustrated herein, there is provided a method for infusing a fluid using an infusion pump including a specially programmed microprocessor; a drip chamber for connection to a source of fluid and to an output tubing; a pumping section including a plurality of fingers and a first actuator; an inlet valve disposed between the drip chamber and the pumping section; and a second actuator, controllable using the microprocessor, including: controlling the first actuator, using the microprocessor, to sequentially displace the plurality of finger to compress a first portion of the output tubing to displace fluid from the drip chamber through the output tubing; and controlling the second actuator, using the microprocessor, to open or close the inlet valve independent of the displacement of the plurality of fingers, or to operate the inlet valve to control a rate of flow of fluid from the drip chamber to the first portion of the output tubing.

According to aspects illustrated herein, there is provided a method for infusing a fluid using an infusion pump including a specially programmed microprocessor; a drip chamber for connection to a source of fluid and to an output tubing; a flow sensor; a pumping section including a plurality of fingers, an outlet valve, and a first actuator; an inlet valve disposed between the drip chamber and the pumping section; and a second actuator, controllable using the microprocessor, including: measuring, using the flow sensor, flow through the drip chamber from the source of fluid; sequentially displacing, using the specially programmed microprocessor and the first actuator, the plurality of finger to displace fluid through the output tubing; and for detection, by the flow sensor, of flow above a predetermined level: closing, using the specially programmed microprocessor and the first actuator, the outlet valve independently of the inlet valve; or closing, using the specially programmed microprocessor and the second actuator, the inlet valve independently of the outlet valve.

According to aspects illustrated herein, there is provided a method for infusing a fluid using an infusion pump including a specially programmed microprocessor; a drip chamber for connection to a source of fluid and to an output tubing; a flow sensor; a pumping section including a plurality of fingers, an outlet valve, and a first actuator for controlling operation of the plurality of fingers; an inlet valve disposed upstream of the pumping section; and a second actuator for operating the inlet valve, including: measuring flow through the drip chamber from the source of fluid using the flow sensor. In a gravity-feed mode, the method includes: controlling, using the specially programmed microprocessor, the first actuator to maintain the plurality of fingers in respective fixed positions and to at least partially open the outlet valve such that a passageway is formed in the output tubing from the drip chamber past the outlet valve; and controlling, using the specially programmed microprocessor and data from the flow sensor including flow measured by the flow sensor, the second actuator to operate the inlet valve to establish flow from the drip chamber to the output tubing at a desired flow rate. In an active pumping mode the method includes: controlling, using the specially programmed microprocessor, the second actuator to open and close the inlet valve; and controlling, using the specially programmed microprocessor, the first actuator to operate the plurality of fingers to displace fluid through the output tubing at the desired flow rate.

According to aspects illustrated herein, there is provided a method for infusing a fluid using an infusion pump including a specially programmed microprocessor; a drip chamber for connection to a source of fluid and to an output tubing; a flow sensor for measuring flow; an inlet valve disposed after the drip chamber; and an actuator for operating the inlet valve. The method includes: accepting, using the microprocessor, data from the flow sensor including flow measured by the flow sensor; and in a gravity-feed mode, controlling, using the microprocessor and the data, the actuator to operate the inlet valve to establish flow from the drip chamber to the output tubing at a desired flow rate.

According to aspects illustrated herein, there is provided a method for infusing a fluid using an infusion pump including a specially programmed microprocessor; a drip chamber for connection to a source of fluid and to an output tubing; a flow sensor for measuring flow from the source of fluid; an element for forcing fluid from the source of fluid; an inlet valve disposed after the drip chamber; and an actuator for operating the inlet valve. The method includes: accepting, using the microprocessor, data from the flow sensor including flow measured by the flow sensor; and in a gravity-feed mode, controlling, the microprocessor and the data, the actuator, the flow sensor to operate the inlet valve to establish flow from the drip chamber to the output tubing at a desired flow rate.

BRIEF DESCRIPTION OF THE DRAWINGS

Various embodiments are disclosed, by way of example only, with reference to the accompanying schematic drawings in which corresponding reference symbols indicate corresponding parts, in which:

FIG. 4 is a table showing example flow pulses and fluid volumes at a flow rate of 0.1 microliter/hour;

DETAILED DESCRIPTION

At the outset, it should be appreciated that like drawing numbers on different drawing views identify identical, or functionally similar, structural elements of the disclosure. It is to be understood that the disclosure as claimed is not limited to the disclosed aspects.

Furthermore, it is understood that this disclosure is not limited to the particular methodology, materials and modifications described and as such may, of course, vary. It is also understood that the terminology used herein is for the purpose of describing particular aspects only, and is not intended to limit the scope of the present disclosure.

Unless defined otherwise, all technical and scientific terms used herein have the same meaning as commonly understood to one of ordinary skill in the art to which this disclosure belongs. It should be understood that any methods, devices or materials similar or equivalent to those described herein can be used in the practice or testing of the disclosure.

Figure 1:
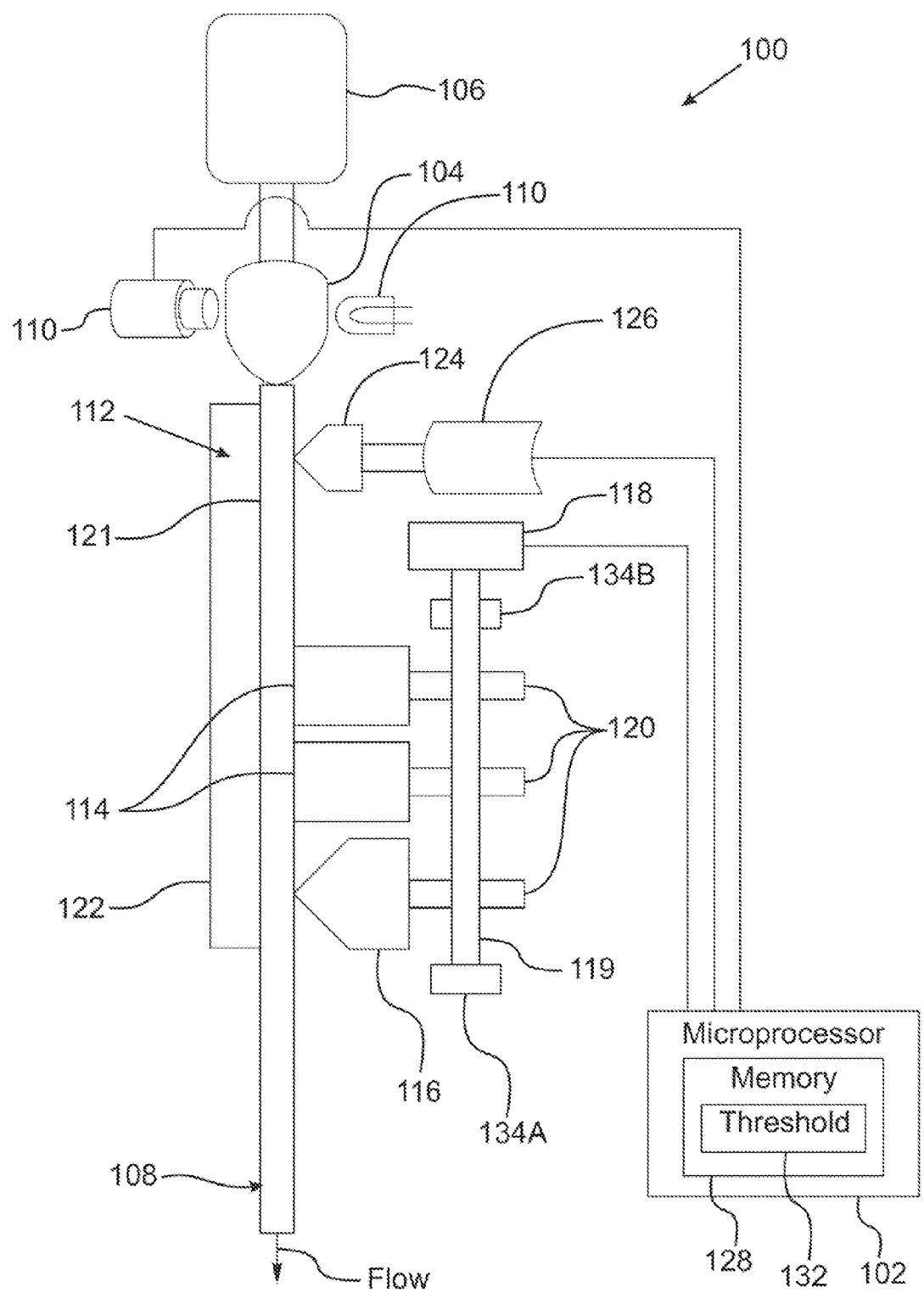
FIG. 1 is a schematic representation of an infusion pump with independent control of inlet and outlet valves.

FIG. 1 is a schematic representation of infusion pump 100 with independent control of inlet an outlet valves. Pump 100 includes specially programmed microprocessor 102, drip chamber 104 for connection to source 106 of fluid and to output tubing 108. The pump includes flow sensor, or flow meter, 110 for measuring flow through the drip chamber, and pumping section 112 including a plurality of fingers 114, outlet valve, or downstream valve, 116, and actuator 118. The pumping section is not limited to a particular number of fingers 114. Actuator 118 is controllable using the microprocessor, to rotate cam shaft 119 and cam lobes 120 such that the cam lobes contact the plurality of fingers to sequentially displace the plurality of finger to compress portion 121 of the output tubing against a support structure, such as supporting platen 122, to displace fluid from the drip chamber through the output tubing and past the outlet valve. Portion 121 also can be considered the portion of the tubing between the inlet and outlet valves. Shaft 119 and cam lobes 120 can displace the fingers in any manner known in the art. Rotation of shaft 119 and cam lobes 120 also controls opening and closing of valve 116.

The pump also includes inlet valve, or upstream valve, 124 disposed between the drip chamber and the pumping section, and actuator 126, controllable using the microprocessor. Actuator 126 is arranged to operate the inlet valve, for example, open or close the inlet valve, or position the inlet valve between open and closed positions, independent of the displacement of the plurality of fingers; or to operate the inlet valve, for example, to position the inlet valve between an open or closed position, to control a rate of flow of fluid from the drip chamber to the output tubing, as further described below.

Figure 2:
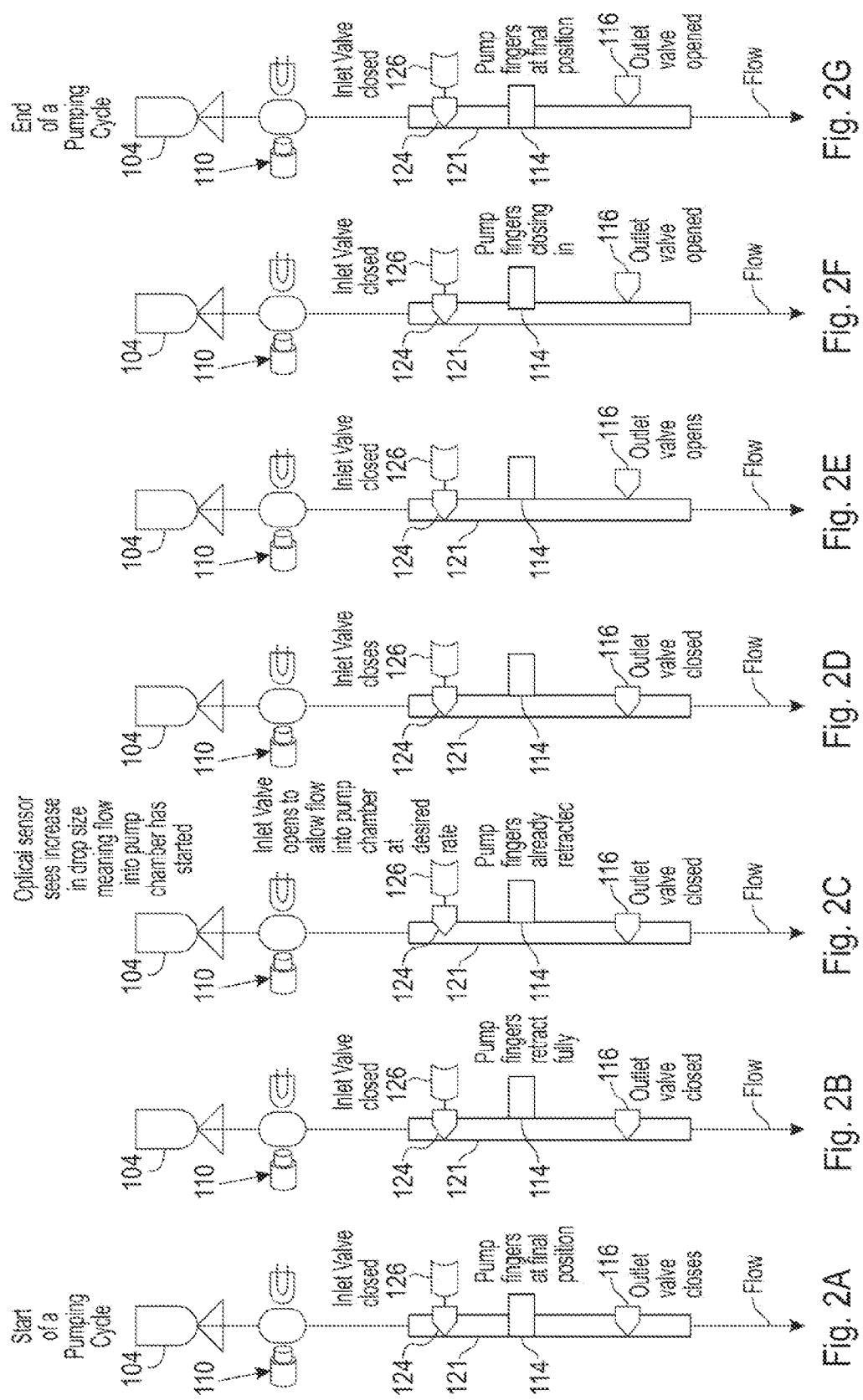
FIGS. 2A through 2G are schematic diagrams illustrating a pumping cycle for the pump shown in FIG. 1.

FIGS. 2A through 2G are schematic diagrams illustrating a pumping cycle for pump 100 shown in FIG. 1. The following should be viewed in light of FIGS. 1 through 2G. Pump 100 enables execution of extremely low continuous flow rates. For example, pump 100 is compliant with the ECRI Institute's Excellent rating for flow continuity at low flow rates, which requires that a period of no flow in an infusion regimen to be less than 20 seconds. In an example embodiment, the specially programmed microprocessor is for implementing the following example infusion scheme, which can be a low flow rate regimen. As shown in FIG. 2A, at the start of a pump cycle for the infusion regimen, the microprocessor controls actuator 126 to close the inlet valve and controls actuator 118 to close the outlet valve and to move the fingers for maximum compression of the tubing by the fingers. As shown in FIG. 2B, actuator 118 retracts the fingers, while the valves remain closed, to create a vacuum in portion 121 of the output tubing, that is, in the passageway formed by portion 121.

As shown in FIG. 2C, the microprocessor controls actuator 126 to displace the inlet valve to flow a specified volume of fluid, as measured by sensor 110, from the drip chamber to portion 121 of the output tubing. By specified volume, we mean a particular volume that is inputted to the microprocessor, stored in memory 128 of the microprocessor, or calculated by the microprocessor. In general, the specified volume is associated with a desired fluid flow to achieve the desired outcome of the infusion scheme. Sensor 110 monitors flow through the drip chamber to portion 121 of the tubing. In an example embodiment, the inlet valve is continuously positionable between a fully closed position and fully open position. For example, a position of the inlet valve is not limited to a series of stepped positions, which would be the case if actuator 126 were a stepper motor. Such continuous positioning greatly increases the accuracy and range of flow rates, from the drip chamber to portion 121, executable using the inlet valve.

As shown in FIG. 2D, after the specified volume of fluid has flowed through the drip chamber to portion 121 of the tubing, for example, as measured by sensor 110, the microprocessor controls actuator 126 to close the inlet valve. As shown in FIG. 2E, the microprocessor then controls actuator 118 to operate the outlet valve, for example, fully opening the outlet valve. As shown in FIG. 2F, the microprocessor controls actuator 118 to displace the plurality of fingers to expel the specified volume of fluid past the outlet valve within a first specified time period. By specified time period, we mean a particular time period that is inputted to the microprocessor, stored in memory by the microprocessor, or calculated by the microprocessor. In general, the specified time period is associated with a desired outcome of the infusion scheme or required operation of the pump. For example, the specified time period can be associated with the ECRI Institute's Excellent rating for flow continuity at low flow rates. As is understood in the art, a time period for infusing the specified volume is usually associated with the specified volume, this time period can be the first specified time period noted above. At the end of the first specified time period, as shown in FIG. 2G, the microprocessor controls actuator 118 to close the outlet valve, completing the pumping cycle.

As noted below, the cycle described above is typically repeated at a particular frequency to attain a desired flow rate over a longer time period.

In an example embodiment, tubing 108 is compressed between the fingers and the supporting platen so that the tubing is partially compressed, reducing the maximum amount noted above, which in turn reduce the volume of fluid entering portion 121 each time the inlet valve is opened. In an example embodiment, tubing 108 has an inner diameter of about 0.1" length L for portion 122 of the tubing (between the inlet and outlet valves) is around 1.25." This configuration results in a maximum volume of about 0.160 milliliter for portion 121. In the example that follows, the maximum volume is reduced to about 0.080 milliliter.

Figure 3:
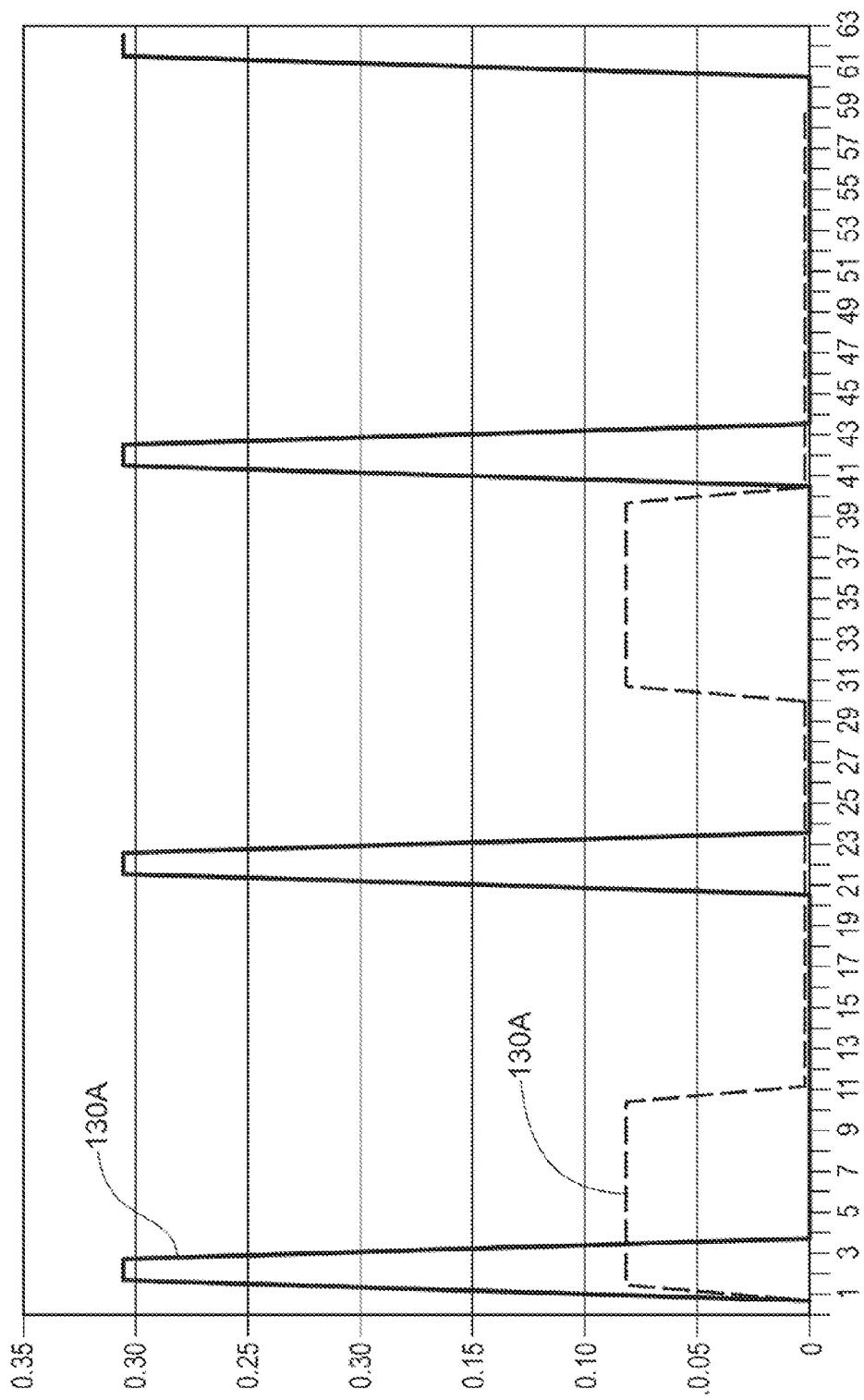
FIG. 3 is a graph showing flow pulses for the pump shown in FIG. 1.

FIG. 3 is a graph showing example flow pulses for pump 100 shown in FIG. 1.

FIG. 4 is a table showing example flow pulses and fluid volumes at a flow rate of 0.1 microliter/hour. The following should be viewed in light of FIGS. 1 through 4. The unit of measurement for the x axis of the graph is second, and the unit of measure for the y axis is microliter of fluid from source 106. The ECRI's Excellent ranking for flow continuity at low flow rate requires that the period of no flow is less than 20 seconds. For example, the time period between FIGS. 2A and 2F must be less than 20 seconds. The microprocessor controls actuator 126 to displace the inlet valve to generate flow pulse 130, that is, to flow a specified volume of fluid from the drip chamber to portion 121 of the output tubing. Flow pulses 130A and B are shown in FIG. 3. As an example, such pulses are generated in the portion of a pumping cycle shown in FIG. 2C. In FIG. 3, the pulses are sized and spaced to implement a flow of 0.1 microliter/hr. It should be understood that other flow pulses are possible, for example, as shown in FIG. 4.

As shown in FIGS. 3 and 4, a variety of pulses 128 can be generated to implement the pumping cycle shown in FIGS. 2A through 2G. For example, pulse 130A is about two second long and the subsequent expelling of fluid from portion 121 is done in about 18 seconds. As another example, pulse 130B is about 10 seconds long and the subsequent expelling of fluid from portion 121 is done in about 10 seconds. Thus, to generate a rate of 0.1 microliter/hr with pulses 130A, pump 100 delivers pulses 130A (FIGS. 2F and 2G) about 164 times per hour, and each pulse delivers about 0.61 microliter of fluid. To generate a rate of 0.1 microliter/hr with pulses 130B, pump 100 delivers pulses 130B (FIGS. 2F and 2G) about 120 times per hour, and each pulse delivers about 0.83 microliter of fluid. It should be understood that combinations of different pulse widths, for example, combinations of pulses shown in FIG. 4, can be used during an infusion regimen. Other combinations of number of pulses and flow pulses are also possible to achieve the desirable flow rate and a no-flow period of less than 20 seconds. For example, for flow rate of 0.1 milliliter/hr or 100 microliter/hr, it is possible to have 10 flow pulses per hour, each of which has 10 microliter of fluid and delivered into the section 121 in less than 20 seconds. The fluid then can be expelled in 5 minutes and 40 seconds.

To provide better flow continuity at low flow rates, the amount of fluid entering portion 121 of the tubing is made smaller than the total volume available in portion 121. For example, when the total volume available is 0.080 milliliter, the amount of fluid entering portion 121, for example, pulses 130, is much less than the available volume, as shown in FIG. 4. Flowing such relatively small amount of fluid can only be done if flow into portion 121 is controlled separately from the movement of the fingers in the pumping chamber, as described above and shown in FIGS. 2A through 2G. Shaft 119 revolves once during the pumping cycle shown in FIGS. 2A-2G. For example, to implement an infusion regimen of 0.1 microliter/hour, shaft 119 revolves once about every 6 minutes.

Using pulses 130A and with a maximum volume available for portion 121 equal to 0.80 milliliter, the amount of fluid entering portion 121 in each pumping cycle is no more that 0.7 percent of the maximum volume for portion 121. Using pulses 130A and with a maximum volume available for portion 121 equal to 0.80 milliliter, the period of no flow for pulses 128A is about 2 seconds or about 10 percent of the maximum no flow period of less than 20 seconds needed for compliance with the ECRI's Excellent ranking for flow continuity at low flow rate. It should be understood that pump 100 is not limited to this ratio of fluid entering portion 121 and maximum volume of portion 121, and that other ratios are possible, for example, as shown in FIG. 4

In contrast, as noted supra, since for a typical prior art peristaltic pump, valves and fingers are all mounted on a single cam shaft, it is not possible to control the amount of fluid entering the chamber independently from the movements of the fingers. Therefore, with a reduced volume of 0.080 milliliter for the output tubing, to generate 0.1 microliter/hr, the output tubing for the prior art pump has to be pumped out in one cycle over a period of 48 min with the attendant problems noted above.

A pumping sequence for an infusion scheme, such as shown in FIGS. 2A through 2G, can be implemented in a periodic sequence, for example, repeating the pumping sequence shown in FIGS. 2A through 2G, to control flow through the drip chamber. For example, a particular flow rate, such as 0.1 microliter/hr, can be executed by repeating the pumping sequence shown in FIGS. 2A through 2G.

Flow sensor 110 in conjunction with actuators 118 and 126 enable redundant shut-off of flow from the drip chamber, for example, in the event of a high flow event. In one embodiment, threshold value 132 for flow detected by sensor 110 is stored in memory element 128. This value can be fixed or can be dependent upon the flow rate for a particular infusion regimen being implemented by the pump, for example, value 132 could be a percentage of the flow rate. The microprocessor uses value 132 for determining if a high flow event is occurring and responds accordingly. For example, for detection, by the flow sensor, of flow above a predetermined level, such as value 132, the microprocessor is for using actuator 118 to close the outlet valve independently of the inlet valve and/or using actuator 126 to close the inlet valve independently of the outlet valve. Thus, even if one or the other of actuators 118 or 126 fails, flow from the drip chamber and portion 121 can be blocked. Value 132 can be received by the microprocessor as input or can be calculated by the microprocessor.

Figure 5:
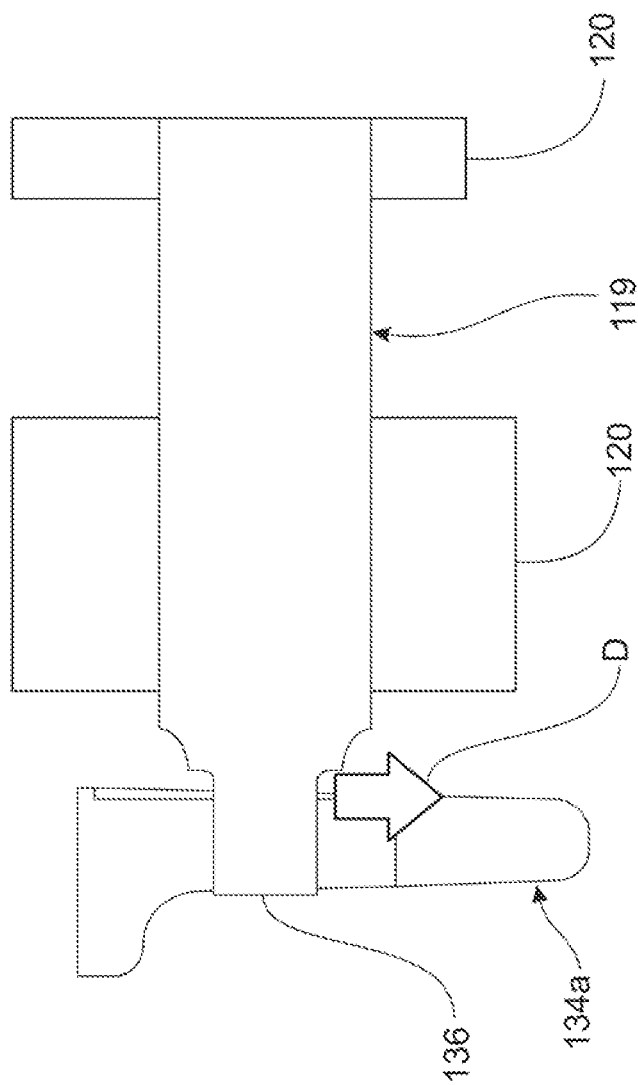
FIG. 5 is a pictorial representation of a portion of the pump shown in FIG. 1 showing a cam shaft bearing.

FIG. 5 is a pictorial representation of pump 100 shown in FIG. 1 showing cam shaft bearing 134. The following should be viewed in light of FIGS. 1 and 5. Cam shaft 119 is supported proximate each end by respective bearings, for example, bearing 134 at the downstream end of the shaft. The bearings hold the shaft in a position that is fixed except for rotation of the shaft. That is, the bearing fix the shaft while enabling rotation of the shaft, for example, to position cam lobes 120A and 120B to operate outlet valve 116 and fingers 114, respectively.

As noted supra, one possible mode of failure for a pump with a cam shaft is the failure of the bearings for the cam shaft. For example, as shown in FIG. 5, if bearing 134 fails, end 136 can shift in direction D, away from the main portion of the pump. One result of the shifting of end 136 is that cam lobes 120 may be displaced far enough from the fingers and the outlet valve such that the cam lobes are no longer able to close the outlet valve or the fingers are no longer able to fully compress portion 121 of the tubing. However, since valve 124 is controlled separately from cam shaft 119 via actuator 126, valve 124 can be actuated to block the tubing regardless of the status of the cam shaft. Thus, even though failure of one or both of the bearings may render fingers 114 and valve 116 unable to control or block flow through the tubing, independently actuated valve 124 is still able to provide flow blockage to prevent a hazardous uncontrolled flow condition.

Pump 100 also provides energy savings. In an example embodiment, pump 100 is switchable between a gravity-feed mode and an active pumping mode. For example, the default mode of operation is the gravity-feed mode and pump 100 operates in this mode unless inadequate flow is detected as described below. The microprocessor operates actuator 118 to maintain the plurality of fingers in respective fixed positions and to open the outlet valve such that a passageway is formed in the output tubing between the inlet and outlet valves. For example, the fingers are displaced so as to compress the tubing to a certain specified extent (partially closing the passageway through portion 121) or are displaced such that the passageway is fully open. The actual location of the fingers and the resultant volume for the passageway can be determined according to the infusion regimen being implemented by pump 100.

The microprocessor controls actuator 126, for example, using feed back from the flow sensor, to operate the inlet valve to establish flow from the drip chamber to the output tubing at a desired flow rate. By desire flow rate, we mean a particular flow rate that is inputted to the microprocessor, stored in memory 128 of the microprocessor, or calculated by the microprocessor. In general, the desired flow rate is associated with a desired outcome of the infusion scheme. As an example, for a particular drug being infused via the infusion scheme, a particular flow rate is needed to attain a desired therapeutic affect.

In an example embodiment, as long as gravity force is sufficient to provide the desire flow rate, the gravity-feed mode is used. For example, as long operation of the input valve is able to provide the desired flow rate, the pump operates in the gravity-feed mode. If operation in the gravity-feed mode is not able to provide the desired flow rate, the pump automatically switches to the active pumping mode. For example, if the inlet valve is fully open and the flow sensor measures flow less than a threshold related to the desired flow rate, for example, a specified percentage of the flow rate, the microprocessor switches to the active pumping mode. In general, the active pumping mode includes coordinated operation of the inlet and outlet valves and the fingers to introduce fluid into portion 121 and expel the fluid past the outlet valve. The pumping cycle shown in FIGS. 2A through 2G is an example, of operation in the active pumping mode. It should be understood that the active pumping mode is not limited to the pumping cycle shown in FIGS. 2A through 2G.

Figure 6:
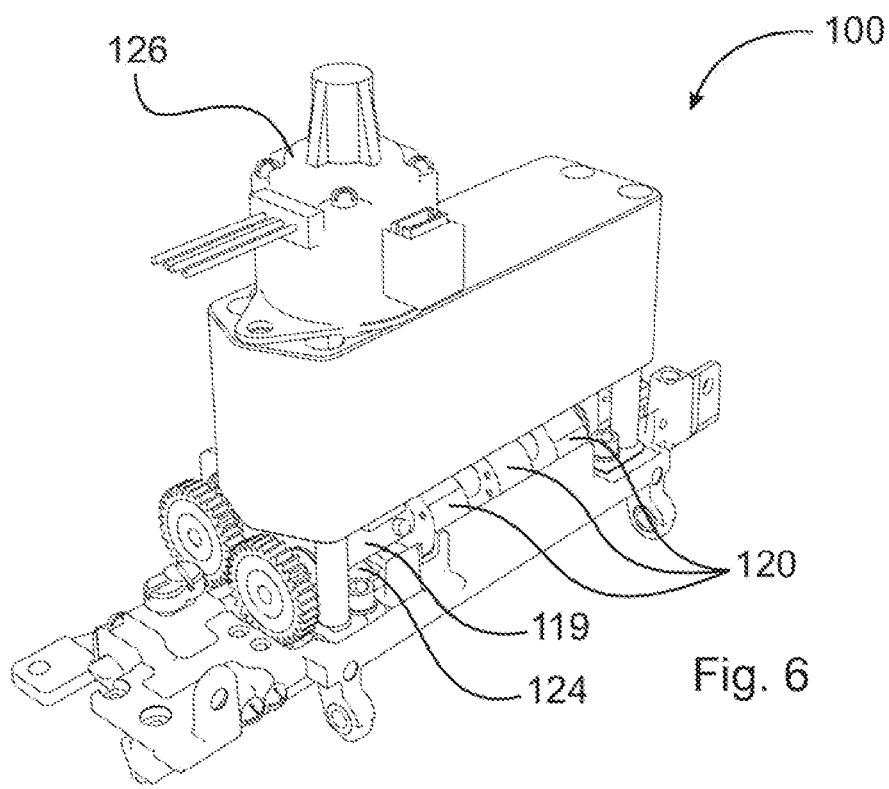
FIG. 6 is a perspective view of an exemplary embodiment of an infusion pump with independent control of inlet and outlet valves and low power operation.

FIG. 6 is a perspective view of an exemplary embodiment of infusion pump 100 with independent control of inlet and outlet valves and low power operation.

Figure 7:
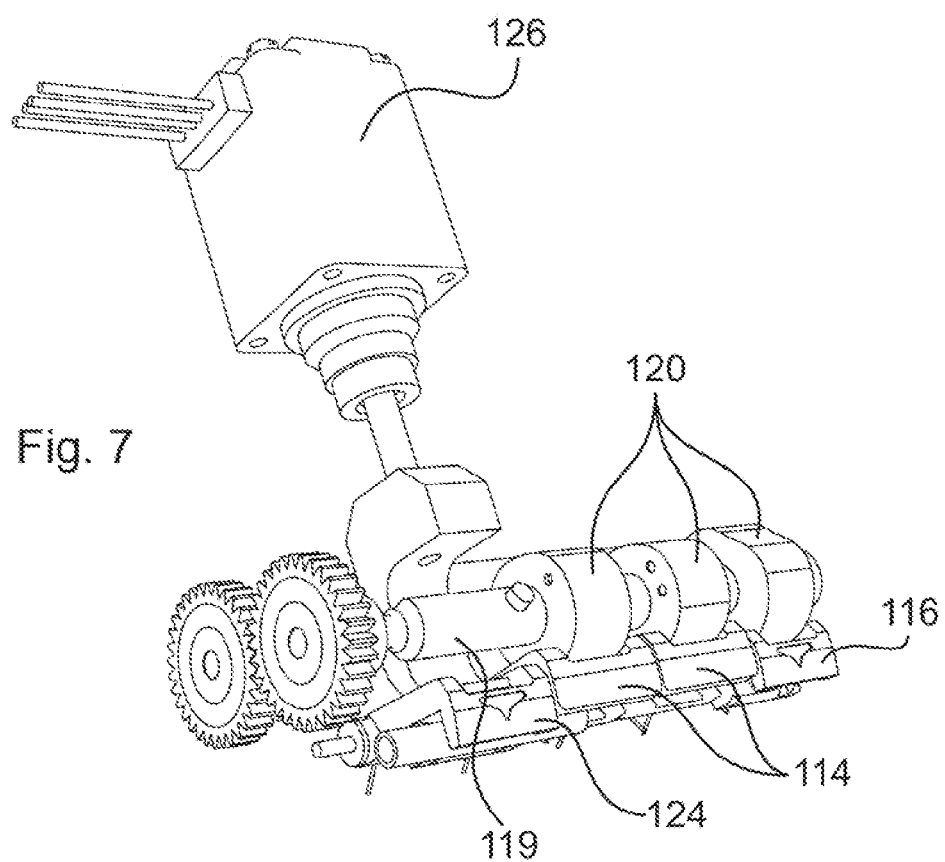
FIG. 7 is a detail of a portion of the pump shown in FIG. 6.

FIG. 7 is a detail of a portion of pump 100 shown in FIG. 6. The following should be viewed in light of FIGS. 6 and 7. FIGS. 6 and 7 depict an exemplary construction of at least portions of a pump with independent control of inlet and outlet valves and other functions described supra. It should be understood that a pump with independent control of inlet and outlet valves and other functions described supra is not limited to the configuration shown in FIGS. 6 and 7.

Figure 8:
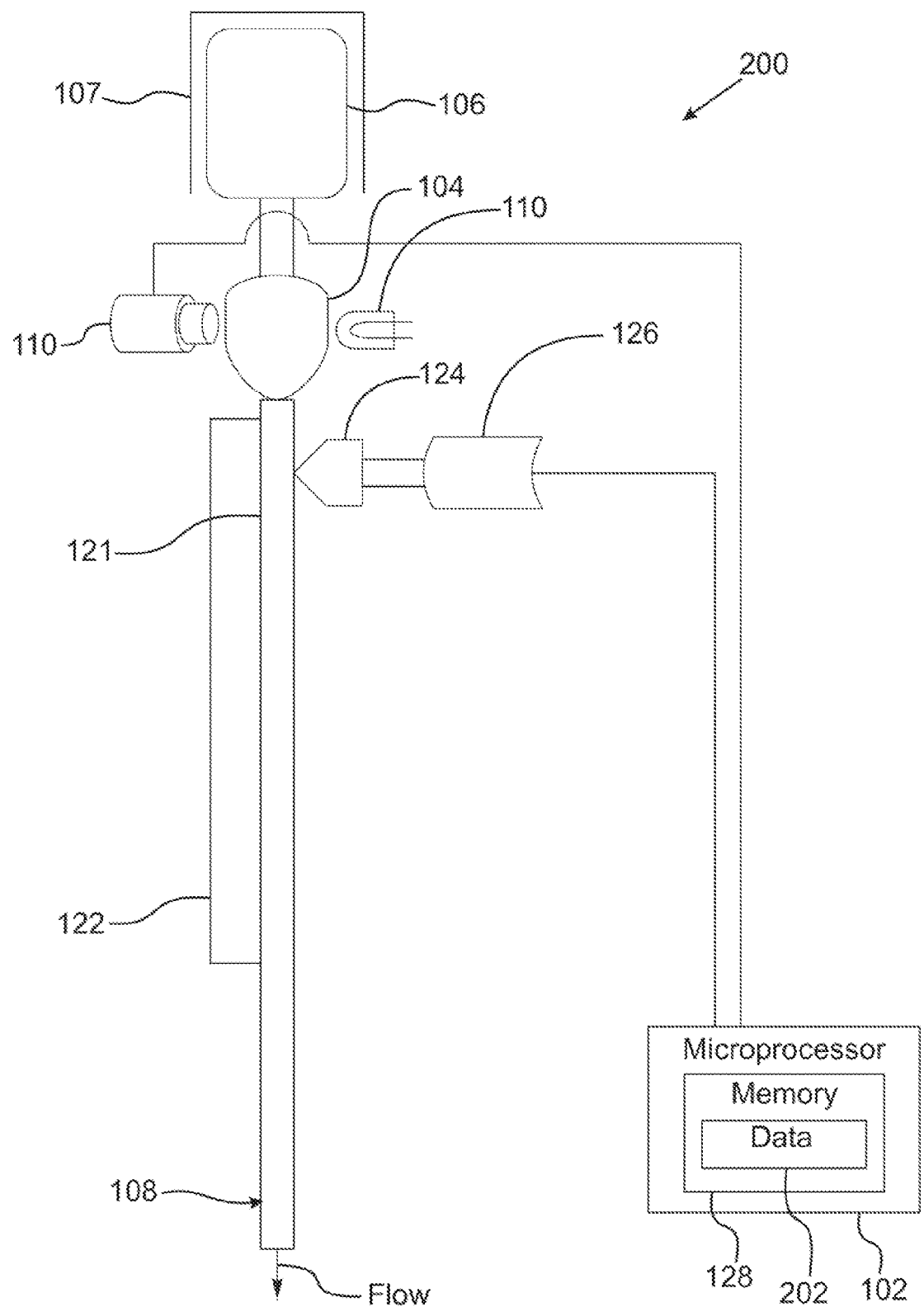
FIG. 8 is a schematic representation of an infusion pump for use in gravity-feed mode.
Figure 9:
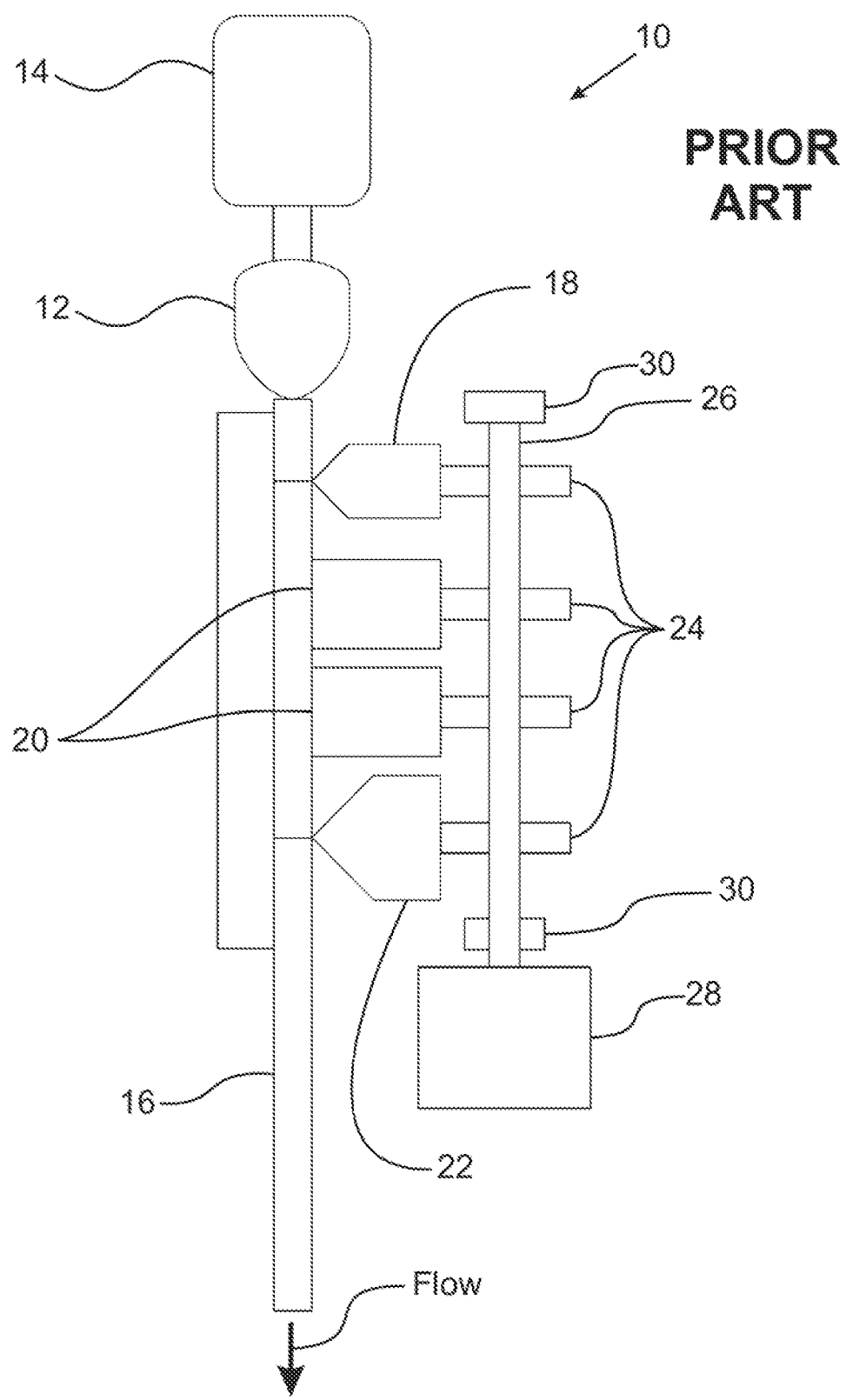
FIG. 9 is a schematic representation of a prior art peristaltic pump.
Figure 10:
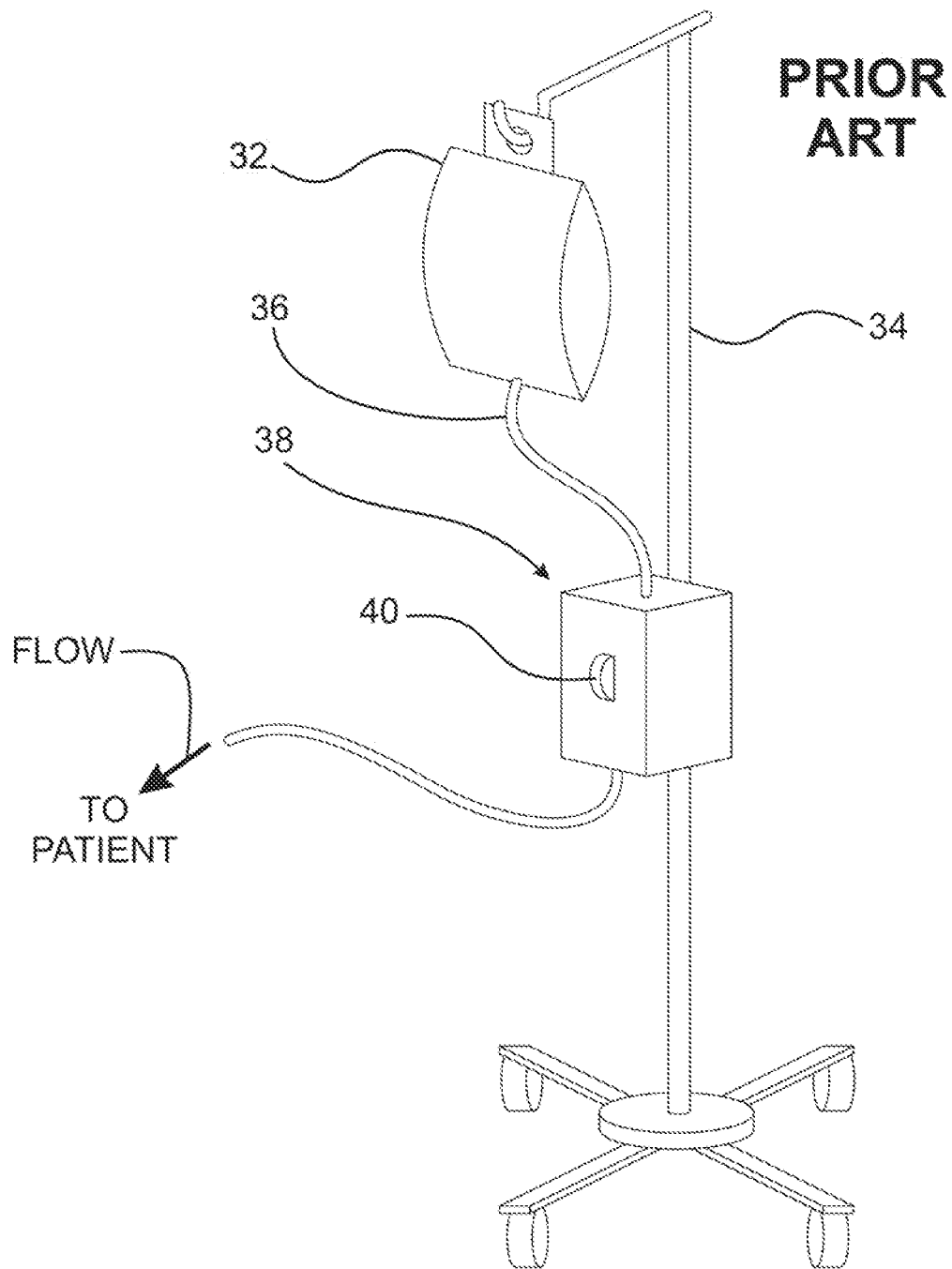
FIG. 10 is a schematic representation of a prior art gravity-feed infusion arrangement.

FIG. 8 is a schematic representation of infusion pump 200 for use in gravity-feed mode. Pump 200 includes specially programmed microprocessor 102 and drip chamber 104 for connection to source 106 of fluid and to output tubing 108. In one embodiment, the source of fluid is a medication bag. In one embodiment, element 107 is used to force fluid from source 106, for example, to squeeze a medication bag, to force fluid out of source 106 and to the drip chamber. For example, in the event that gravitational force on the fluid in source 106 is not sufficient to overcome backpressure in tubing 108, for example, due to a patient to whom the tubing is connected, element 107 can be used to provide the extra force needed to overcome the back pressure. Any device known in the art can be used for element 107.

The pump includes flow sensor, or flow meter, 110 for measuring flow through the drip chamber, and inlet valve 124 disposed downstream of the drip chamber. Actuator 126 is controllable using the microprocessor to regulate flow through tubing 108. Actuator 126 is arranged to operate the inlet valve, for example, open or close the inlet valve, or position the inlet valve between open and closed positions, to control a rate of flow of fluid from the drip chamber to the output tubing. Thus, pump 200 is configured to operate in gravity-feed mode, for example, pump 200 does not include a pumping section, such as pumping section 112 for pump 100 in FIG. 1, to actively transport fluid from source 106 through tubing 108. In the gravity-feed mode, the flow can be via gravitation force alone or can be via a combination of gravitation force and force applied by element 107.

In gravity-feed mode, the microprocessor is arranged to control the actuator, using data from the flow sensor including flow measured by the flow sensor, to operate the inlet valve to establish flow from the drip chamber to the output tubing at a desired flow rate. That is, the microprocessor accepts data 202 from the flow sensor including flow measured by the flow sensor and controls, using the data, the actuator to operate the inlet valve to establish flow from the drip chamber through the output tubing at a desired flow rate. The discussion for pump 100 regarding a desired flow rate is applicable to FIG. 8 and pump 200. Pump 200 is arranged to occlude the tubing, via valve 124, in response to emergency or alarm conditions.

Although pumps 100 and 200 have been shown with a particular configuration of components, it should be understood that pumps 100 and 200 are not limited to the particular configuration of components shown and that other configurations of components are possible.

It will be appreciated that various of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

What we claim is:

1. An infusion pump for controlling a flow condition of a source of fluid and delivered to a user through an output tubing, the pump comprising:
   a computer processor;
   a first actuator configured for displacing at least one finger for compressing a first portion of the output tubing to deliver the source of fluid to the user;
   a second actuator configured for selectively operating an inlet valve of the infusion pump to control the flow condition of the source of fluid to the first portion of the output tubing; and
   an outlet valve is disposed downstream of the first portion of the output tubing, and the output tubing includes a second portion between the inlet and outlet valves, said outlet valve being controlled by said first actuator, wherein, using the processor, the first actuator controls the displacement of the at least one finger and the operation of said outlet valve independently from the inlet valve, and the second actuator controls the operation of the inlet valve independently from the at least one finger.

2. The infusion pump of claim 1, wherein the source of fluid is connected to a drip chamber, the inlet valve is disposed between the drip chamber and the first portion of the output tubing, and is arranged for compressing the output tubing to control the flow condition of the source of fluid through the output tubing.

3. The infusion pump of claim 1, wherein said fingers are constructed and arranged to generate a pumping action by compressing the first portion of the outlet tubing.

4. The infusion pump of claim 1, wherein the source of fluid is connected to a drip chamber, the second actuator operates the inlet valve for enabling flow of a predetermined amount of the source of fluid from the drip chamber to the second portion of the output tubing while controlling the first actuator to close the outlet valve, and maintaining the at least one finger in a respective fixed position.

5. The infusion pump of claim 1, wherein the source of fluid is connected to a drip chamber, the second actuator operates the inlet valve for disabling flow of the source of fluid from the drip chamber to the second portion of the output tubing after a predetermined amount of the source of fluid has flowed to the second portion of the output tubing.

6. The infusion pump of claim 1, wherein the first actuator operates the outlet valve for displacing the at least one finger to expel a predetermined amount of the source of fluid past the outlet valve within a first specified time period, and to close the outlet valve at the end of the first specified time period.

7. The infusion pump of claim 1, further comprising a flow sensor configured for measuring a flow rate of the source of fluid, and memory configured for storing a threshold value of the flow rate, wherein the inlet valve is operated based on the threshold value.

8. The infusion pump of claim 7, wherein the inlet valve is operated based on the flow rate independently from the outlet valve, and the outlet valve is operated based on the flow rate independently from the inlet valve.

9. The infusion pump of claim 1, wherein the infusion pump operates in at least one of: a gravity-feed mode and an active pumping mode based on a flow rate of the source of fluid.

10. The infusion pump of claim 1, wherein a pumping section of the pump includes an outlet valve, and the pumping section with the at least one finger is configured for acting on the first portion of the output tubing located between the inlet valve and the outlet valve, using a common linkage for controlling the at least one finger and the outlet valve.

11. A computer-implemented method for controlling a flow condition of a source of fluid and delivered to a user through an output tubing, the method comprising:
displacing at least one finger for compressing a first portion of the output tubing to deliver the source of fluid to the user using a first actuator;
selectively operating an inlet valve of the infusion pump to control the flow condition of the source of fluid to the first portion of the output tubing using a second actuator;
disposing an outlet valve downstream of the first portion of the output tubing, and including a second portion of the output tubing between the inlet and outlet valves;
controlling, using a computer processor, the displacement of the at least one finger and the outlet valve independently from the inlet valve using the first actuator; and
controlling, using the computer processor, the operation of the inlet valve independently from the at least one finger and the outlet valve using the second actuator.

12. The method of claim 11, further comprising disposing the inlet valve between a drip chamber connected to the source of fluid and the first portion of the output tubing, and arranging the inlet valve for compressing the output tubing to control the flow condition of the source of fluid through the output tubing.

13. The method of claim 11, further comprising operating said fingers to create a pumping action by partially compressing the first portion of output tubing, and operating said first and second valves to periodically block the first portion of output tubing under the control of the processor.

14. The method of claim 11, further comprising operating, using the second actuator, the inlet valve for enabling flow of a predetermined amount of the source of fluid from a drip chamber connected to the source of fluid to the second portion of the output tubing while controlling the first actuator to close the outlet valve, and maintaining the at least one finger in a respective fixed position.

15. The method of claim 11, further comprising operating, using the second actuator, the inlet valve for disabling flow of the source of fluid from a drip chamber connected to the source of fluid to the second portion of the output tubing after a predetermined amount of the source of fluid has flowed to the second portion of the output tubing.

16. The method of claim 11, further comprising operating, using the first actuator, the outlet valve for displacing the at least one finger to expel a predetermined amount of the source of fluid past the outlet valve within a first specified time period, and to close the outlet valve at the end of the first specified time period.

17. The method of claim 11, further comprising measuring, using a flow sensor, a flow rate of the source of fluid, and storing a threshold value of the flow rate in memory, and operating the inlet valve based on the threshold value.

18. The method of claim 17, further comprising operating the inlet valve based on the flow rate independently from the outlet valve, and operating the outlet valve based on the flow rate independently from the inlet valve.

19. The method of claim 11, further comprising operating the infusion pump in at least one of: a gravity-feed mode and an active pumping mode based on a flow rate of the source of fluid.

20. The method of claim 11, further comprising providing a pumping section having an outlet valve, wherein the pumping section with the at least one finger is configured for acting on the first portion of the output tubing located between the inlet valve and the outlet valve.

* * * * *